United States Patent [19]

Waterbury et al.

[11] Patent Number: 4,857,474
[45] Date of Patent: Aug. 15, 1989

[54] PHYCOERYTHRINS USEFUL IN FLUORESCENT CONJUGATES

[75] Inventors: John B. Waterbury; Stanley W. Watson, both of Woods Hole, Mass.; Alexander N. Glazer, Orinda; Linda J. Ong, Hayward, both of Calif.

[73] Assignee: Research Corporation, New York, N.Y.

[21] Appl. No.: 717,634

[22] Filed: Mar. 29, 1985

[51] Int. Cl.$^4$ .............. G01N 33/566; G01N 33/533; G01N 33/542; C12N 1/20

[52] U.S. Cl. .................... 436/501; 530/370; 530/387; 436/519; 436/536; 436/537; 436/546; 436/800; 435/822; 435/252.1

[58] Field of Search ............... 530/370, 387.9; 435/7, 435/29, 253, 822; 436/501, 519, 536, 537, 546, 800

[56] References Cited

U.S. PATENT DOCUMENTS

| | | | |
|---|---|---|---|
| 4,520,110 | 5/1985 | Stryer et al. | 436/501 |
| 4,542,104 | 9/1985 | Stryer et al. | 436/537 X |
| 4,666,862 | 5/1987 | Chan | 436/501 |

OTHER PUBLICATIONS

Ong, L. J. et al, *Science*, vol. 224, Apr. 6, 1984, pp. 80–83.
Alberte, R. S. et al, *Plant Physiol.*, vol. 75, 1984, pp. 732–739.
Kursar, T. A. et al, *Proc. Natl. Acad. Sci., USA*, vol. 78, No. 11, 1981, pp. 6888–6892.
"Immunoassay Techniques with Fluorescent Phycobiliprotein Conjugates", M. N. Kronick, and P. D. Grossman, *Clinical Chemistry* 29: 1582–1586 (1983).
Comparative Biochemistry of Photosynthetic Light–Harvesting Systems, A. N. Glazer, *Ann. Rev. Biochem.*, 52: 125–157 (1983).
"Fluorescent Phycobiliprotein Conjugates for Analysis of Cells and Molecules", V. T. Oi, A. N. Glazer and L. Stryer, *J. Cell. Bio.*, 93: 981–986 (1982).
Phycobilisomes: Structure and Dynamics, A. N. Glazer, *Ann. Rev. Microbiol.*, 36: 173–198 (1982).
Structure and Evaluation of Photosynthetic Accessary Pigment Systems with Special Reference to Phycobiliproteins, A. N. Glazer, In: "The Evaluation of Protein Structure and Function", Academic Press, 1980, pp. 221–244.
"Identification and Enumeration of Marine Chroococcoid Cyanobacteria by Immunofluorescence", L. Campbell, E. J. Carpenter, and V. J. Iacono, *Appl. Environ. Microbiol.*, 46: 533–559 (1983).
"Dual Immunofluorescent Analysis of Human Peripheral Blood Lymphocytes", J. T. Thornthwaite, D. Seckinger, E. V. Sugarbaker, P. K. Rosenthal, and D. A. Vazquez, *Amer. J. Clin. Path.*, 82: 48–56 (1983).
"Phycoerythrins of the Red Alga *Callithamnion*", M. H. Yu, A. N. Glazer, K. G. Spencer, and J. A. West, Plant Physiol., 68: 482–488 (1981).
"Fluorescent Tandem Phycobiliprotein Conjugates", A. N. Glazer, L. Stryer, Biophysical Journal, 43: 383–386 (1983).
"Phycoerythrocyanin and Phycoerythrin: Properties and Occurence in Cyanobacteria", D. A. Bryant, *Gen. Microbiol.*, 128: 835–844 (1982).

Primary Examiner—Johnnie R. Brown
Assistant Examiner—Jeremy M. Jay
Attorney, Agent, or Firm—Scully, Scott Murphy & Presser

[57] ABSTRACT

This invention provides a class of phycoerythrins useful in diagnostic and detection protocols wherein a fluorescent label is required. The unique spectral properties of the phycoerythrins described herein provide for increased sensitivity and alternative uses in assays employing them.

16 Claims, 5 Drawing Sheets

PHYCOERYTHRINS USEFUL IN FLUORESCENT CONJUGATES

This invention was made in part with support from National Science Foundation Grants PCM-82-08158 and OCE 82-14889.

FIELD OF THE INVENTION

This invention relates to a novel class of phycoerythrins. More specifically, this invention relates to phycoerythrins as the fluorescent components of fluorescent conjugates useful as reagents in the analysis and separation of molecules and cells.

BACKGROUND OF THE INVENTION

Phycobiliproteins are a family of colored proteins which serve as components of the light-harvesting apparatus of a variety of cyanobacteria and red algae. In vivo the phycobiliproteins occur as macromolecular assemblages, known as phycobilisomes, attached to thylakoid membranes. The structure and comparative biochemistry of phycobilisomes and phycobiliproteins have been the subject of numerous reviews (see for example: Glazer, A. N., *Ann. Rev. of Microbiol* 36:173-98 (1982) and Glazer, A. N., *Biochem. Biophys. Acta* 768: 29-51 (1984). Briefly, phycobiliproteins (or as they are also known, biliproteins) possess a basic monomer structure comprised of two dissimilar polypeptides (i.e. an $\alpha,\beta$ subunit structure). A third subunit ($\gamma$) as well as various other linker polypeptides may also be associated with the basic monomer or multiples thereof. The characteristic absorbance of the various biliproteins is due in large measure to the existence of open-chain tetrapyrrole prosthetic groups which are covalently attached to the $\alpha$, $\beta$ or $\gamma$ subunits by means of at least one thioether bond. A number of factors dictate the particular spectroscopic properties that individual types of biliproteins will display, these include the number and type of prosthetic groups, the conformational relationship between the prosthetic groups and the subunit to which they are attached and changes in the structural environment due to the formation of molecules of higher aggregation states.

FIG. 1 illustrates the number and types of bilin prosthetic groups among the subunit of various biliproteins and Table 1 summarizes some properties of common phycobiliproteins.

TABLE 1
PROPERTIES OF PHYCOBILIPROTEINS

| Biliprotein | Distribution[1] | Absorption maxima in the visible[2] (nm) | Fluorescence emission maximum[2] (nm) | PUB/PEB Ratio |
|---|---|---|---|---|
| Allophycocyanin B | C,R | 671 618 | 680 | — |
| Allophycocyanin | C,R | 650 | 660 | — |
| C-Phycocyanin | C,R | 620 | 637 | — |
| R-Phycocyanin | R | 617 555 | 63 | — |
| Phycoerythrocyanin | C | 568 590(s) | 625 | — |
| C-Phycoerythrin | C | 565 | 577 | — |
| b-Phycoerythrin | R | 545 563(s) | 570 | — |
| B-Phycoerythrin | R | 545 563 498(s) | 575 | 0.06 |
| R-Phycoerythrin | C,R | 567 538 498 | 578 | 0.36 |

[1]C = cyanobacteria; R = red algae.
[2]For a given biliprotein, the exact positions of the absorption and emission maxima vary somewhat depending on the organism that serves as the source of the protein and on the method of purification.

As can be seen from Table 1, red algae possess phycoerythrins displaying visible absorption spectra with peaks at about 566 nm and peaks or shoulders at about 540 and 500 nm with varying relative intensities. Red algal phycoerythrins carry two types of covalently attached tetrapyrrole prosthetic groups, phycoerythrobilin (PEB) and phycourobilin (PUB). The PEB groups give rise to the 566- and 540-nm peaks, and the PUBs give rise to the 500-nm peak. In contrast, phycoerythrins purified from cyanobacteria isolated from soil or fresh water contain only PEB groups and do not exhibit the 500-nm peak. The cyanobacterium *Gloeobacter violaceus* does contain a phycoerythrin with both PEB and PUB chromophores, but the organism is atypical in other respects as well (Bryant, D. A. et al., *Arch Microbiol.* 129:190 (1981) and Rippka R, et al, *Arch. Microbiol.* 100–419 (1974). The difference in the bilin composition of red algal and cyanobacterial phycoerythrins may be related to the changing nature of solar radiation as it penetrates seawater. Marine algae are exposed to maximum transmission of light at approximately 500 nm and the presence in these organisms of a photosynthetic accessory pigment (PUB) that absorbs maximally at this wavelength appears to be more than coincidental.

Unicellular cyanobacteria containing phycoerythrin have been observed in abundance among marine phytoplankton (Waterbuty, J. B., et al, *Nature* 277:293 (1977)), and these organisms make a major contribution to the primary productivity in the ocean. Although the phycoerythrin of several of these organisms is of the ordinary cyanobacterial type (C-phycoerythrin), it is interesting that many strains contain phycoerythrins with both PEB and PUB chromophores (Fujita, Y. and S. Shimura, *Plant Cell Physiol* 15:9393 (1974) Alberte et al., *(Plant Physiol.* 74: 732–737 (1984). Kusar et al. *Pro. Nat'l. Acad. Sci. USA* 78: 6888–6897 (1981)). Phycoerythrin purified from a marine *Synechococcus* contains the highest content of PUB of any known phycoerythrin (Ong, et al. *Science* 224: 80–83, (1984).

In a recent survey of marine *Synechococcus* spp. Alberte et al, (*Plant Physiol* 74: 732–739 (1984) identified two apparently novel types of *Synechococcus* based upon their spectral and biochemical properties. The first type (Type II-PE) possesses a phycoerythrin exhibiting a single broad absorption maximum at 551 nm and a fluorescence emission peak at 570 nm. The second type (Type I-PE) is characterized by phycoerythrins exhibiting adsorption maxima at 558 and at 500 nm and a fluorescence emission peak at 560 nm. When absorption measurements are made after acid-urea treatment Type II-PE displays an absorption maximum at 558 nm while the Type I displays maxima at 558 and 500. The absorption at 558 is presumably due to phycoerythrobilin (PEB) however the "classic" PEB as present in the C-, R- and b- PEB exhibit at maximum absorbance at 550 nm in acid urea. The shift of 8 nm to red is unexplained and the authors refer to this species as "PEB-like". The absorption maximum at 500 nm in the Type I-PE is ascribed to the phycourobilin (PUB) chromophore. The ratio of PUB/PEB-like chromophores in Type I-PE is 1.3/4.9=0.26.

The utility of phycobiliproteins as components of reagents for fluorescence analysis of molecules and cells has been described by Oi, V. T. et al., (*J. Cell. Biol.* 93:981 (1983)) by Stryer et al., (Eur. Pat. Appln. 0.076694, Apr. 4, 1983) and by Kronick, M. N. and Grossman, P. D., (*Clin. Chem.* 29 (9): 1582 (1983)). Oi, et al. and Stryer et al. disclose the use of phycobiliprotein conjugated to immunoglobulins, protein A, biotin and avidin and the application of these conjugates to fluorescence-activated cell sorting, fluorescence microscopy, and fluorescence immunoassays. R-phycoerythrin (from *Gastroclonium coulteir*), C-phycocyanin (from Synechococcus), allophycocyanin (from *Anabaena variabilis*) and B-phycoerythrin (from *Porphyridium cruentum*) were employed in forming the conjugates. Kronick and Grossman (supra) disclose the use of B-phycoerythrin (from *P. cruentum*) coupled to rabbit anti-human IgG in solid phase "sandwich-type" immunoassays. These references to the extent they provide the background necessary for the skilled artisan to practice this invention are incorporated herein by reference.

This invention is predicated upon the discovery of a unique new type of phycoerythrin exhibiting particular advantageous spectral properties and that inter alia under appropriately selected conditions the sensitivity of assays employing this phycoerythrin is nearly doubled.

BRIEF DESCRIPTION OF THE INVENTION

This invention provides a phycoerythrin isolatable from a marine cyanobacterium characterized by an absorption maxima at about 542 and about 492 and a 542/492 ratio of less than about 2.0 and PUB/PEB ratio of greater than 0.36.

In a further embodiment this invention provides a fluorescent compound comprising a biliprotein covalently conjugated to a member of a specific binding pair consisting of ligand and receptor characterized in that the biliprotein displays absorption maxima at about 542 and at about 492, a 542/492 ratio of less than about 2.0, a PUB/PEB ratio of greater than about 0.36 and an emission maximum at 560 nm.

In a further embodiment this invention provides a a fluorescent immunoassay method employing as a reagent a fluorescent biliprotein conjugated to a member of a specific binding pair consisting of ligand and receptor. The improvement which comprises employing a biliprotein having absorption maxima at about 542 and at about 492, a 542/492 ratio of less than about 2 and a PUB/PEB ratio of greater than 0.36 and an emission maximum at 560 nm.

In a further embodiment this invention provides a biologically pure culture of a marine cyanobacterium capable of producing a phycoerythrin wherein said phycoerythrin has absorption maxima at about 542 and about 492, a 542/492 ratio of less than about 2.0, a PUB/PEB ratio of greater than 0.36, and an emission maximum at about 560 n.

In a further embodiment this invention provides a fluorescent activated cell sorting method employing a fluorescent biliprotein the improvement which comprises employing a biliprotein having absorption maxima at about 542 and at about 492, a 542/492 ratio of less than 2, a PUB/PEB ratio of greater than 0.36 and an emission maximum at 560 nm.

In a further embodiment this invention provides a method of detecting cells or cellular components by means of fluorescent microscopy employing a fluorescent biliprotein the improvement which comprises employing a biliprotein having absorption maxima at about 542 and at about 492, a 542/492 ratio of less than about 2, a PUB/PEB ratio of greater than 0.36 and an emission maximum at 560 nm.

DETAILED DESCRIPTION OF THE DRAWINGS

FIG. 1 provides a diagrammatic representation of the various subunit structures of a members of the phycobiliproteins.

Figure 4:
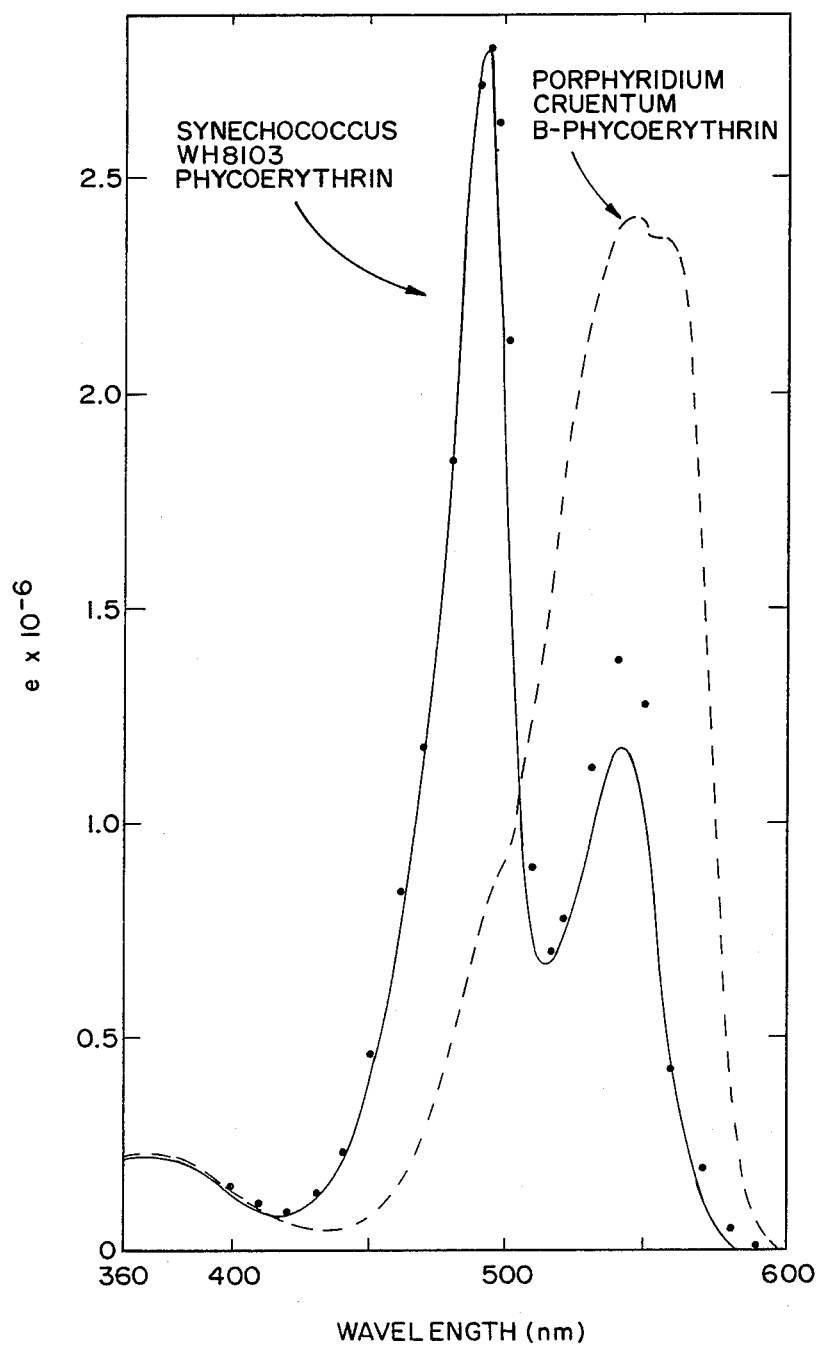

FIG. 4 illustrates the molar absorption spectra of WH8103 and *Porphyridium cruentum* phycoerythrins. Closed circles represent values from an excitation spectrum of WH8103 phycoerythrin determined for emission at 595 nm. The absorption and excitation spectra were normalized at 492 nm.

Figure 5:
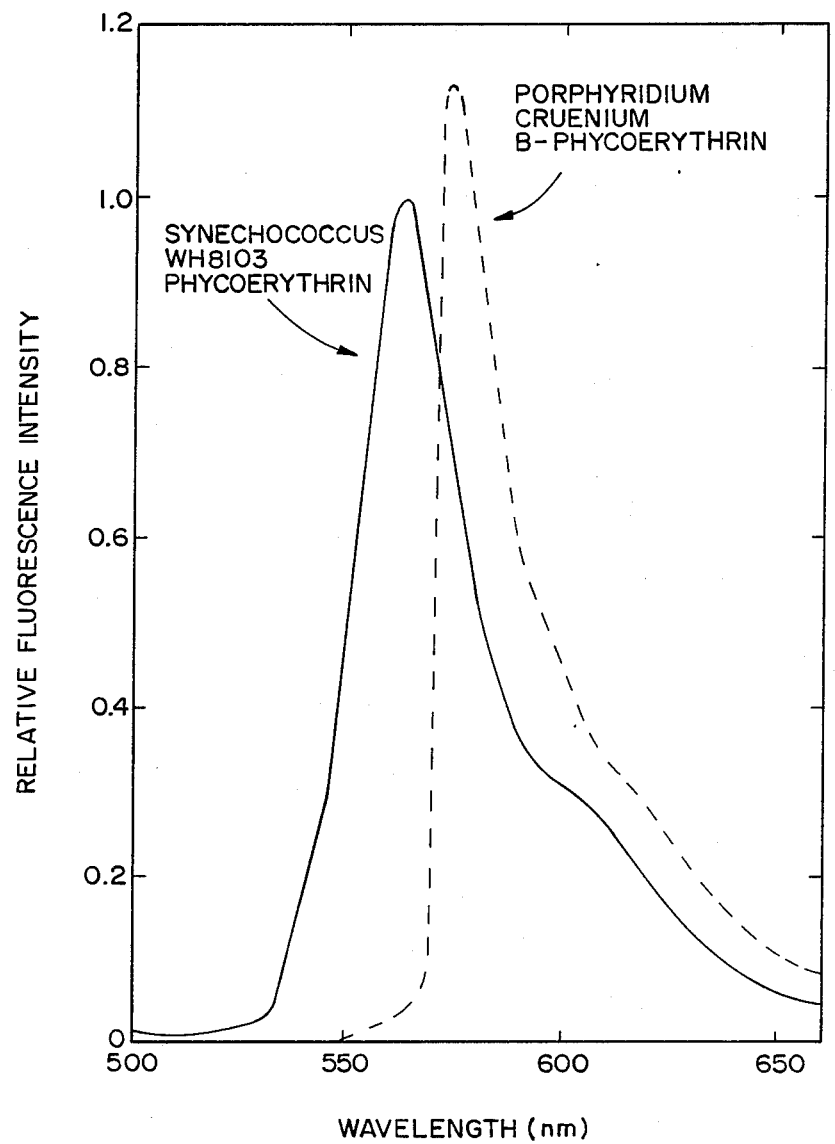

FIG. 5 illustrates the fluorescence emission spectra of WH8103 and *Porphyridium cruentum* phycoerythrins. Excitation was at 490 nm and sample absorbance at the excitation wavelength was 0.05 $cm^{-1}$.

DETAILED DESCRIPTION OF THE INVENTION

This invention provides a novel group of phycobiliproteins (biliproteins) useful as fluorescent moieties in conjugates comprising said biliprotein and a member of a specific binding pair, said binding pair consisting of ligands and receptors.

The ligand may be any compound of interest for which there is a complementary receptor. For the most part, the ligands of interest will be compounds having physiological activity, either naturally occurring or synthetic. One group of compounds will have a molecular weight in the range of about 125 to 2,000, more usually from about 125 to 1,000, and will include a wide variety of drugs, small polypeptides, vitamins, enzyme substrates, coenzymes, pesticides, hormones, lipids, etc. These compounds for the most part will have at least one heteroatom, normally oxygen, sulfur or nitrogen and may be alipatic, alicyclic, aromatic, or heterocyclic or combinations thereof. Illustrative compounds include epinephrine, prostaglandins, thyroxine, estrogen, corticosterone, ecdysone, digitoxin, aspirin, pencillin, hydrochlorothiazide, quinidine, oxytocin, somatosatin, diphenylhydantoin, retinol, vitamin K, cobalamine, biotin and folate.

Compounds of greater molecular weight, generally being 5,000 or more molecular weight include poly(amino acids)-polypeptides and proteins-polysaccharides, nucleic acids, and combinations thereof e.g. glycosaminoglycans, glycoproteins, ribosomes, etc. Illustrative compounds include albumins, globulins, hemogloblin, surface proteins on cells, such as T- and B-cells e.g. Jeu, Thy, Ia, tumor specific antigens, $\alpha$-fetoprotein, retinol binding protein, C-reactive protein, enzymes, toxins, such as cholera toxin, diphtheria toxin, botulinus toxin, snake venom toxins, tetrodotoxin, saxitoxin, lectins, such as concanavalin, wheat germ agglutinin, and soy bean agglutinin, immunoglobulins, complement factors, lymphokines, mucoproteins, polysialic acids, chitin, collagen, keratin, etc.

Receptors particularly useful for practicing this invention include antibodies (monoclonal or polyclonal) specifically reactive with the ligand of interest, cell surface antigens, protein A from *Staphylococcus aureus*, or avidin, however, any receptor specifically reactive with the ligand of interest would be useful.

Depending upon the molecule being labeled, a wide variety of linking groups may be employed for conjugating the biliprotein to the ligand or receptor. For the most part, with small molecules, those under 2,000 molecular weight, the functional group of interest for linking will be carbonyl, either an aldehyde to provide for reductive amination or a carboxyl, which in conjunction with carbodiimide or as an activated ester e.g. N-hydroxy succinimide, will form a covalent bond with the amino groups present in the biliprotein; a thio ester or disulfide, where the biliprotein may be modified with an activated olefin and a mercapto group added or activated mercapto groups joined e.g. Elman's reagent; isothiocyanate; diazonium; nitrene or carbene. Where the biliproteins are conjugated with a protein, various bifunctional reagents may be employed, such as dialdehydes, tetrazonium salts, diacids, or the like, or alternatively, one or both of the two proteins involved may be modified for conjugation to the other protein, for example, a mercapto group may be present or be introduced on one protein and an activated olefin e.g. maleimide introduced into the other protein.

Specific details of conjugate formation may be found in European Patent Application No. 076695 to Stryer et al. published Apr. 13, 1983 the contents of which are incorporated herein by reference.

Phycobiliproteins useful for practicing this invention may be easily isolated from microbes common in the marine environment. Particularly preferred microbes are marine cyanobacteria of the genus Synechococcus.

The marine planktonic Synechococcus, characterized by its small size (0.7×1.5 μm), a predominance of phycoerythrin making the cells fluorescent orange, and elevated salt requirements for growth, is both widespread and abundant in oceanic waters (Waterbury et al. Nature 277: 293-294 (1979); Johnson and sieburth, *Limnol. Oceanorg.* 24: 928-955 (1979)). Current observations indicate that it is present throughout the year in the tropical oceans at concentrations ranging from $10^3$ to $10^4$ cells $ml^{-1}$. In the temperature oceans its presence is seasonal. It is abundant during the summer months often reaching concentrations in excess of $10^5$ cells $ml^{-1}$. In the winter Synechococcus disappears when the water temperature falls below 5° C. and does not reappear in the spring until the water temperature reaches 12° C. A preliminary survey taken in December 1980 at the McMurdo Station on the Ross Ice Shelf in Antarctica failed to reveal Synechococcus. This observation, coupled with the fact that Synechococcus disappears in the temperature oceans when the water temperature falls below 5° C., suggests that this cyanobacterium is excluded from the polar seas.

Documentation of the role Synechococcus as an oceanic primary producer is facilitated by its small size which makes it possible to separate this organism from larger eucaryotic phytoplankters by sequential filtration through a series of filters of decreasing pore size. A single fraction can be obtained containing between 50-80% of the in situ concentration of Synechococcus cells while excluding all other phytoplankters. By comparing the amounts of radioactive sodium bicarbonate assimilated by aliquots of unfiltered seawater and the fraction containing the natural population of Synechococcus it is possible to estimate the portion of primary productivity attributable to Synechococcus.

The contribution of Synechococcus to primary productivity has been documented in two areas: The relatively nutrient-rich waters near Woods Hole, Massachusetts and in the oligotrophic waters of the northern Sargasso Sea. In Woods Hole Harbor Synechococcus is responsible for 3 to 7% of the total primary productivity, whereas in the northern Sargasso Sea 15 to 20% of the primary productivity is attributable to this cyanobacterium.

The relative role of Synechococcus is greater in oligotrophic waters than in more nutrient-rich inshore waters. However, the amount of carbon fixed $cell^{-1}hr^{-1}$ does not vary dramatically between these regions, indicating that Synechococcus does equally well in both areas with the difference in relative importance being that the eucaryotic phytoplankters are not as successful in oligotrophic waters as they are in nutrient-rich areas.

To illustrate the relative ease with strains containing phycobiliproteins useful in practicing this invention may be recovered, Table 2 summarizes the results of ocean samplings over a period of three different years and at a variety of locations. The details of culturing and screening the microorganisms are provided in the Examples which follow.

TABLE 2

| Synechococcus Strains* Useful for Practicing the | | | | | |
|---|---|---|---|---|---|
| Strain No. | Source and date of isolation | Axenic | DNA base ratio (% G + C) | Swimming motility | Phycoerythrin ratio of peak heights 542/492 |
| WH 8103 | 28° 30'N, 67° 23'W 3/17/81 | + | 58.9 | + | 0.4 |
| WH 8102 | 22° 29'N, 65° 36'W 3/15/81 | + | 60.4 | − | 0.5 |
| WH 8107 | 39° 28'N, 70° 27'W 6/81 | − | | − | 0.58 |
| WH 8013 | 34° N, 65° W 7/7/80 | − | | − | 0.54 |
| WH 8112 | 36° N, 66° W 10/81 | + | 59.8 | + | Variable+ |
| WH 8113 | 36° N, 66° W 10/81 | + | 60.5 | + | 1.0 |
| WH 8011 | 34° N, 65° W 7/80 | + | 59.3 | + | 1.19 |
| WH 8109 | 39° 28'N, 70° 27'W 6/81 | + | | − | 1.13 |

TABLE 2-continued

Synechococcus Strains* Useful for Practicing the

| Strain No. | Source and date of isolation | Axenic | DNA base ratio (% G + C) | Swimming motility | Phycoerythrin ratio of peak heights 542/492 |
|---|---|---|---|---|---|
| WH 8201 | 20° 44'N, 109° 04'W 5/6/82 | — | | — | 1.06 |
| WH 8108 | 39° 28'N, 70° 27'W 6/81 | — | | — | 1.3 |
| WH 8020 | 38° 40'N, 69° 19'W 6/26/80 | + | 57.5 | — | 1.4 |

*Cell size. Diameter 0.6–0.9 um; length: 1.2–1.8 um. White light: 1.4; green light: 1.5; red light: 0.58.

Even though strains yielding phycobiliproteins useful in practicing the subject invention can be routinely isolated from nature, a deposit of a strain in a public depository was made as described below.

Deposit of a Strain Useful in Practicing the Invention

A deposit of a biologically pure culture of the following strain was mailed to the American Type Culture Collection, 12301 Parklawn Drive, Rockville, Md. on Mar. 20, 1985 the accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture (s) of the same taxonomic description.

| Strain | ATCC No. |
|---|---|
| WH 8103 | 53061 |

The following Example illustrates the subject invention but should not be construed as limiting same.

EXAMPLE I

This example describes the evaluation and characterization of a phycoerythrin derived from a strain of Synechococcus.

Synechococcus strain WH8103 (ATCC: 53061) was cultured in a natural seawater-based medium at 23° C. in a Fernbach flask; continuous warm white light (intensity of about $8 \times 10^{-6}$ E/M$^2$-sec) was supplied, and the entire mixture was swirled once daily. The culture medium contained (milligrams per liter) NaNO$_3$, 750.0; K$_2$KPO$_4$, 15.3; Na$_2$CO$_3$, 10.0; EDTA-Na$_2$, 5.0; (milliliters per liter) trace metal mix, 1; seawater 877; deionized water, 120; vitamin mix, 2. Trace metal mix contained (grams per liter) ZnSO$_4$·7H$_2$O, 0.222; MnCl$_2$·4H$_2$O, 1.40; Co(NO$_3$)$_2$·6H$_2$O, 0.025; Na$_2$MoO$_4$·2H$_2$O, 0.39; citric acid monohydrate, 6.25; ferric ammonium citrate, 6.00. Seawater was diluted with deionized water to 30 parts per thousand salinity. Vitamin mix contained (grams per liter) thiamine, 2.0; B$_{12}$, 0.001; biotin, 0.001. The stock solution was sterilized by passage through a 0.2-μm Nuclepore filter. The medium was autoclaved and allowed to cool to room temperature before addition of the vitamin mix. Cells were harvested by centrifugation from approximately 3-week-old cultures that had reached an absorbance of about 0.15 at 750 nm. Phycobilisomes were prepared as described by Yamanaka et al. (*J. Biol. Chem.* 253: 8303 (1978)) with the exception that the breakage buffer contained 0.01M EDTA and 0.001 M phenylmethylsulfonyl fluoride. Preparation of phycoerythrin was as follows. Phycobilisomes were dialyzed against a 0.05M sodium phosphate—0.001M NaN$_3$ buffer (pH 7.0) for at least 3 hours to dissociate the particles and reduce the sucrose concentration. Ammonium sulface was then added to 65 percent saturation, and the solution was allowed to stand overnight at 4° C. The precipitate was collected by centrifugation, resuspended in the pH 7.0 buffer, and dialyzed exhaustively against the same buffer at 4° C. The solution was then layered on density gradients of 0.2, 0.4, 0.5, 0.8, and 1.0M sucrose in the pH 7.0 buffer in 2.2-ml increments. Ultracentrifugation was performed in a Spinco SW41 rotor at 66,000 g$_{av}$ for 22.5 hours at 18° C., during which phycoerythrin sedimented down the gradient farther than the other biliproteins. The phycoerythrin zone was collected, and the protein was recovered by precipitation with ammonium sulfate as described above. The precipitate was dissolved in 0.001M sodium phosphate-0.1M NaCl (pH 7.0) at 4° C. and dialyzed against the same buffer. The solution was applied to a column of hydroxylapatite (settled bed volume of 0.4 ml per milligram of protein), equilibrated with 0.001M sodium phosphate- 0.1M NaCl (pH 7.0), and developed with buffers of increasing phosphate concentration. Pure phycoerythrin was eluted with 0.03 to 0.04M sodium phosphate-0.1 M NaCl (pH 7.0).

Figure 1:
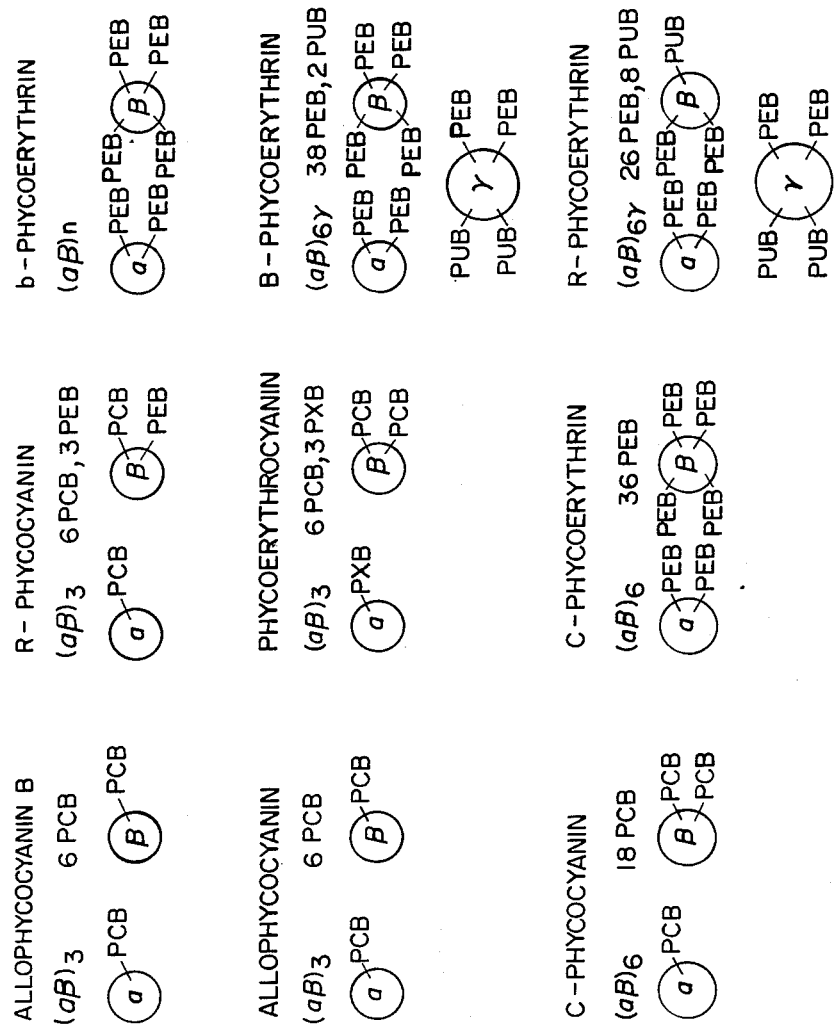
Figure 2:
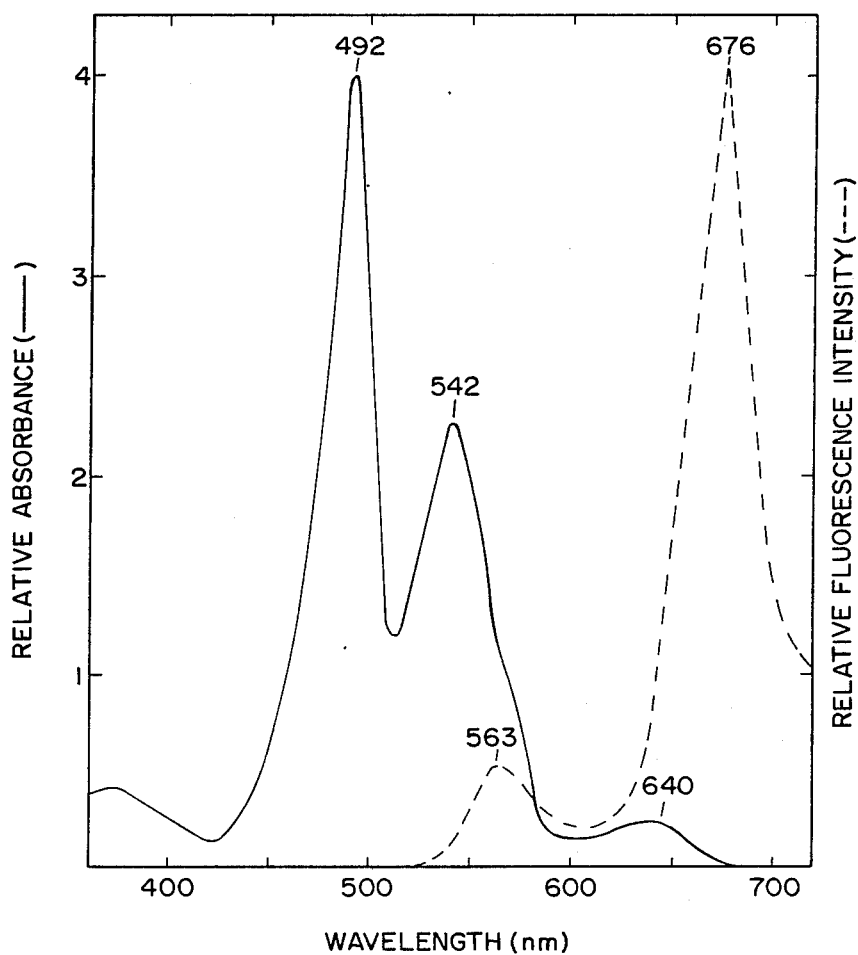
FIG. 2 illustrates the absorption and fluorescence emission spectra of Synechococcus WH8103 phycobilisomes in 0.75M sodium potassium phosphate buffer (pH 8.0). Excitation for the emission spectrum was at 490 nm, and the excitation and emission monochromator slits were set at 4-nm bandpass.

The absorption and fluorescence emission spectra of WH8103 physobilisomes are shown in FIG. 2. The emission spectrum is similar to the spectra observed for cyanobacterial phycobilisomes of various biliprotein compositions. Energy absorbed by the PUB chromophores of WH8103 phycoerythrin is transferred efficiently to the terminal energy acceptors of the phycobilisome, which are responsible for the 676-nm emission peak. The small emission peak at 563 nm represents the direct emission of fluorescence from phycoerythrin.

Several properties of purified WH8103 phycoerythrin were characterized. The molecular weight of the native protein was determined by ultracentrifugation on linear sucrose density gradients by the method of Martin and Ames (*J. Biol. Chem.* 236: 1372 (1961)). WH8103 phycoerythrin settled as a single zone with a sedimentation velocity identical to that of *Porphyridium cruentum* B-phycoerythrin, for which a molecular weight of 240,000 has been determined (Glazer, A. N. and C. S. Hixson, *J. Biol. Chem.* 252: 32 (1977)).

Figure 3:
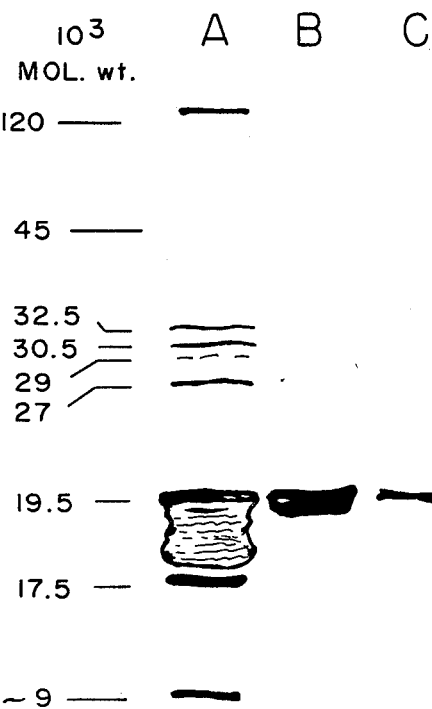
FIG. 3 illustrates the pattern of polyacrylamide gel electrophoresis in the pesence of sodium dodecyl sulfate of (lane A) *Anabaena variabilis* phycobilisome polypeptides as molecular weight markers; (lane B) WH8103 phycoerythrin; (lane C), a smaller amount of WH8103 phycoerythrin than applied in lane B to allow discrimination between the $\alpha$ and $\beta$ subunits.

On polyacrylamide gel eletrophoresis in the presence of sodium dodecyl sulfate (FIG. 3). WH8103 phycoerythrin showed a polypeptide composition similar to that of red algal B- and R-phycoerythrins with α and β subunits of 19 to 20 kilodaltons and three bands in the γ subunit region of about 29 kilodaltons. Comparison of the amino acid composition of WH8103 phycoerythrin with that of P. cruentum B-phycoerythrin (Table 3) reveals a rough similarity between these two proteins.

| Amino acid | Value (mean ± S.E.M.)* | |
|---|---|---|
| | WH8103 | P. cruentum |
| Lys | 85.0 ± 0.8 | 84.2 ± 2.1 |
| His | (14.0) | 13.8 ± 0.7 |
| Arg | 115.0 ± 0.6 | 117.4 ± 2.6 |
| Asp | 221.5 ± 0.8 | 228.3 ± 1.6 |
| Thr** | 104.7 | 75.1 |
| Ser** | 171.4 | 172.8 |
| Glu | 157.7 ± 0.6 | 152.9 ± 2.1 |
| Pro | 97.9 ± 1.9 | 63.6 ± 2.4 |
| Gly | 184.8 ± 0.5 | 151.3 ± 2.8 |
| Ala | 309.0 ± 0.9 | 320.3 ± 6.9 |
| ½ Cys | 34.4 ± 0.1 | 24.5 |
| Val | 142.1 ± 1.4 | 167.7 ± 3.1 |
| Met | 46.5 ± 0.1 | 53.4 ± 0.3 |
| Ile | 98.8 ± 0.5 | 98.4 |
| Leu | 170.0 ± 0.4 | 154.1 ± 3.1 |
| Tyr | 83.2 ± 0.7 | 96.0 ± 1.6 |
| Phe | 46.5 ± 0.2 | 45.1 ± 1.2 |
| Trp | (6.0) | 6.0 |

*Values obtained from three analyses.
**Values obtained by linear extrapolation to time zero.

The bilin composition of WH8103 phycoerythrin was determined by the method of Glazer and Hixson (*J. Biol. Chem.* 252: 32 (1977)) from spectra of solutions of known protein content in 8M urea (pH 1.9). Molar extinction coefficients (E) used for PUB in this solvent were 104,000 (490 nm) and 0 (550 nm); those for PEB in the same solvent were 13,700 (490 nm) and 49,000 (550 nm). These measurements indicated the presence of 20.5 PUB and 13 PEB groups per 240,000 daltons of WH8103 phycoerythrin. Both red algal B- and R-phycoerythrins carry 34 bilins per 240,000 daltons.

The molar absorption spectrum of WH8103 phycoerythrin is compared to that of *P. cruentum* B-phycoerythrin in FIG. 4. The numerous PUB chromophores in WH8103 phycoerythrin give rise to the sharp peak at 492 nm. *Prophyridium cruentum* B-phycoerythrin contains only two PUB groups. The fluorescence emission spectra for 490 nm excitation of WH8103 and *P. cruentum* phycoerythrins are compared in FIG. 5. Quantum yield determination were performed on these two proteins with a Perkin-Elmer MPF44B spectrofluorimeter equipped with a DCSU02 corrected spectra unit, a 500-nm blazed emission grating, and a Hamamatsu R926 phototube. Rhodamine-101 in methanol was used as a primary standard with a quantum yield (Q) of 1.0 as in the method of Karstens and Kobs (*J. Phys. Chem.* 84: 1871 (1980)). Measurements were performed at a sample absorbance of 0.05 cm$^{-1}$ at the excitation wavelength of 490 nm. For WH8103 phycoerythrin, Q=0.50; for *P. cruentum* B-phycoerythrin, Q=0.57. Upon 532 nm excitation with a mode-locked Nd$^{3+}$: YAG laser, the fluorescence of WH8103 phycoerythrin exhibited single-component exponential decay with a lifetime of 1.85±0.8 nsec. This indicates that the procedure used leads to a preparation of phycoerythrin of uniform size. A lifetime of 2.1±0.1 nsec has been determined for *P. cruentum* B-phycoerythrin under similar conditions.

All of these observations indicate that WH8103 phycoerythrin is similar in its molecular and energy transfer properties to phycoerythrins obtained from red algae. However, the distinctive feature of this protein—its high content of PUB—makes this phycoerythrin valuable as a fluorescent tag for analytical use.

The value of biliprotein conjugates as reagents for fluorescence-activated cell sorting and analysis, fluorescence microscopy, and fluorescence immunoassay has been shown (Oi, V. T. et al. *J. Cell. Bio.* 93: 981 (1982)). Phycoerythrin conjugates emit in the orange region of the spectrum, where background autofluorescence of cells is much lower than at shorter wavelengths. The fluorescence intensity of such conjugates is also higher than that of fluorescein conjugates. For example, for excitation at the argon-ion laser line (488 nm), E=2.78×10$^6$ and Q=0.5 for WH8103 phycoerythrin; the corresponding values for fluorescein are E=8×10$^4$ and Q=0.9. Therefore, a solution of WH8103 phycoerythrin excited at 488 nm has a fluorescence intensity 19.3 times higher than that of an equimolar solution of fluorescein. For typical R-phycoerythrins available from numerous red algae, E=1.28×10$^6$. Assuming that these proteins have a fluorescence quantum yield similar to that of B-phycoerythrin (Q=0.57), the corresponding fluorescence intensity ratio for these proteins relative to fluorescein is 10.1. A phycoerythrin-fluorescein intensity ratio of 10 was measured when an equimolar solution of *Gastroclonium coulteri* R-phycoerythrin and fluorescein were fluxed through a cell sorter (Oi, V. T. et al., supra). Hence, WH8103 phycoerythrin conjugates would nearly double the sensitivity of assays employing this class of biliproteins.

The phycoerythrins of this invention possess another characteristic, namely an emission maximum at 560 nm, which makes these compounds particularly useful as reagents for flow cytometry, fluorescence microscopy and the like. As mentioned previously, conjugates containing the biliproteins of this invention may be used to fluorescent stain cells. The cells may then be evaluated by microscopy or in a fluorescence activated cell sorter (FACS). When two or more biliprotein conjugates are used together in a double staining protocol the emission maximum of the fluorescers should be separated to permit their discrimination. It is, of course, possible to use the conjugates of this invention in combination with fluorescers other than biliproteins, such as fluorescein, dansyl, umbelliferone, benzoxadiozoles, pyrenes, rose bengal, etc. For example, propidium iodide is used in flow cytometry to discard dead cells and to stain DNA. This fluorescer excites well at 488 nm and has a fluorescence emission maximum near 600 nm. The phycoerythrins currently available have fluorescence emission maxima between 570–578 nm. The overlap in this range is sufficient to preclude the use of propidium iodine and phycoerythrin together as fluorescer in flow cytometry. The phycoerythrin described herein possessing an emission maximum 560 nm can be used in combination with propidium iodide due to elimination of the overlapping fluorescence of the two moieties.

What is claimed is:

1. In a fluorescent immunoassay method employing as a reagent a fluorescent biliprotein isolated from a marine cyanobacterium of the genus Synechococcus, conjugated to a member of a specific binding pair selected from the group consisting of ligand and receptor the improvement which comprises employing a biliprotein having absorption maxima at about 542 and at about 492, a 542/492 ratio of less than about 2, a PUB/PEB ratio of greater than 0.36, and an emission maximum at 560 nm.

2. A phycoerythrin isolated from a biologically pure culture of marine cyanobacterium of the genus Synechococcus, said phycoerythrin characterized by absorption maxima at about 542, and at about 492, a 542/492 ratio of less than 2.0, a PUB/PEB ratio of greater than 0.36 and an emission maximum at 560 nm.

3. The phycoerythrin according to claim 2 wherein said cyanobacteria is Synechococcus WH8103 (ATCC 53061).

4. A phycoerythrin according to claim 2 wherein said 542/492 ratio is between 0 and about 1.9.

5. A phycoerythrin according to claim 4 wherein said 542/492 ratio is from about 0.4 to about 1.4.

6. A phycoerythrin according to claim 5 wherein said 542/492 ratio is about 0.4.

7. A fluorescent compound comprising a biliprotein isolated from a marine cyanobacterium of the genus Synechococcus, covalently conjugated to a member of a specific binding pair selected from the group consisting essentially of a ligand and a receptor, characterized in that the biliprotein essentially displays absorption maxima at about 542, and at about 492, a 542/492 ratio of less than about 2.0, a PUB/PEB ratio of greater than 0.36 and an emission maximum at 560 nm.

8. The compound according to claim 7 wherein said member is a receptor.

9. The compound according to claim 8 wherein said receptor is a cell surface antigen.

10. The compound according to claim 8 wherein said receptor is an antibody.

11. The compound according to claim 7 wherein said member is a ligand.

12. In a fluorescent activated cell sorting method employing a fluorescent biliprotein isolated from a marine cyanobacterium of the genus Synechococcus, the improvement which comprises employing a biliprotein having an absorption maxima at about 542 and at about 492, a 542/492 ratio of less than about 2, a PUB/PEB ratio of greater than 0.36 and an emission maximum at 560 nm.

13. In a method of detecting cells or cellular components by means of fluorescent microscopy employing a fluorescent biliprotein isolated from a marine cyanobacterium of the genus Synechococcus, the improvement which comprises employing a biliprotein having absorption maxima at about 542 and at about 492, a 542/492 ratio of less than about 2, and a PUB/PEB ratio of greater than 0.36 and an emission maximum at 560 nm.

14. A biologically pure culture of marine cyanobacterium of the genus Synechococcus producing a phycoerythrin wherein said phycoerythrin has an absorption maxima at about 542 and about 492, a 542/492 ratio of less than about 2.0 a PUB/PEB ratio of greater than 0.36, and an emission maximum at about 560 nm.

15. The cyanobacterium according to claim 14 wherein said cyanobacterium is a member of the genus Synechococcus.

16. The cyanobacterium according to claim 15 wherein said cyanobacterium is ATCC 53061.

* * * * *

UNITED STATES PATENT AND TRADEMARK OFFICE
CERTIFICATE OF CORRECTION

PATENT NO. : 4,857,474

DATED : August 15, 1989

INVENTOR(S) : John P. Waterbury, et al.

It is certified that error appears in the above-identified patent and that said Letters Patent is hereby corrected as shown below:

Title page:

In the Abstract, line 2: "in" should read as --for--

Column 2, line 14: "100-419" should read as --100:419--

Column 2, line 24: "Waterbuty" should read as --Waterbury--

Column 2, line 32: "15:9393" should read as --15:939--

Column 9, line 10: insert --TABLE 3-- and add new paragraph to read: -- Comparison of the amino acid compositions of WH8103 phycoerythrin and *Porphyridum cruentum* B-phycoerythrin. Lyophilized protein samples (~0.25 mg) were dissolved in 6N HCl containing 0.15 (weight to volume) percent phenol and hydrolyzed in vacuo at 110°C for 24, 48, and 72 hours. A value of residues of His and 6 residues of Trp and a molecular weight of 240,000 were assumed for WH8103 phycoerythrin. Data on *P. cruentum* B-phycoerythrin are from (4). S.E.M., standard error of the mean.--

Signed and Sealed this

Eighth Day of January, 1991

Attest:

HARRY F. MANBECK, JR.

*Attesting Officer*   *Commissioner of Patents and Trademarks*